(12) United States Patent
Becker et al.

(10) Patent No.: US 7,884,728 B2
(45) Date of Patent: Feb. 8, 2011

(54) MEDICAL MONITORING SYSTEM AND PROCESS FOR PROCESSING ALARM SIGNALS

(75) Inventors: Uwe Becker, Eichenau (DE); Jürgen Kelch, Bad Schwartau (DE); Hartmut Schmidt, Heilshoop (DE)

(73) Assignee: Dräger Medical GmbH, Lübeck (DE)

( * ) Notice: Subject to any disclaimer, the term of this patent is extended or adjusted under 35 U.S.C. 154(b) by 667 days.

(21) Appl. No.: 11/850,903

(22) Filed: Sep. 6, 2007

(65) Prior Publication Data

US 2008/0094227 A1 Apr. 24, 2008

(30) Foreign Application Priority Data

Oct. 18, 2006 (DE) ................ 10 2006 049 137

(51) Int. Cl.
*G08B 23/00* (2006.01)
(52) U.S. Cl. ............... 340/573.1; 340/506; 340/539.12
(58) Field of Classification Search ............ 340/539.1, 340/539.12, 506, 500, 573.1; 705/1–3; 600/300, 600/301
See application file for complete search history.

(56) References Cited

U.S. PATENT DOCUMENTS

| 4,522,213 A | 6/1985 | Wallroth et al. | |
| 5,920,263 A | 7/1999 | Huttenhoff et al. | |
| 7,443,302 B2 * | 10/2008 | Reeder et al. | 340/573.1 |
| 7,649,449 B2 * | 1/2010 | Fenske et al. | 340/506 |

FOREIGN PATENT DOCUMENTS

| DE | 3302321 | 5/1984 |
| DE | 19634675 B4 | 3/1998 |
| DE | 10217107 | 11/2002 |
| EP | 0911775 B1 | 4/1999 |
| JP | 2001126174 A | 5/2001 |

* cited by examiner

*Primary Examiner*—Anh V La
(74) *Attorney, Agent, or Firm*—McGlew & Tuttle, P.C.

(57) ABSTRACT

A monitoring system and process is provided for at least two medical apparatuses, which can send at least one alarm signal each. At least one alarm unit is connected to these apparatuses, wherein the alarm unit has at least one processing unit, a memory unit and an output unit. The processing unit assigns priorities to the alarm signals, and an assignment list of the distribution of the priorities of the individual alarms is stored in the memory unit.

17 Claims, 2 Drawing Sheets

MEDICAL MONITORING SYSTEM AND PROCESS FOR PROCESSING ALARM SIGNALS

CROSS REFERENCE TO RELATED APPLICATIONS

This application claims the benefit of priority under 35 U.S.C. §119 of German Patent Application DE 10 2006 049 137.8 filed Oct. 18, 2006, the entire contents of which are incorporated herein by reference.

FIELD OF THE INVENTION

The present invention pertains to a medical monitoring system and to a process for processing alarm signals.

BACKGROUND OF THE INVENTION

Various medical apparatuses, which detect and analyze various physiological parameters of patients, are used in medical establishments. These may be, for example, blood pressure, body temperature, the oxygen saturation in the blood, carbon dioxide concentration in the breathing gas, etc. Rapid recognition of critical patient values and malfunctions of the apparatuses must take place in intensive care, in particular. The users of the apparatuses are alerted to these critical states by means of alarms. All these apparatuses have signal units for the visual or audio indication of an alarm and have an alarm handling of their own. Above all, the acknowledgment of the alarm states take place directly at the apparatus. A plurality of apparatuses may trigger an alarm independently from one another at the same time in critical situations of the patient. The alarms must be acknowledged or turned off individually at the apparatuses. In acute situations, in which rapid response is mandatory, there frequently is no time for turning off the individual alarms. The result is a cacophony of alarms, which further increases the stress of the medical staff.

A device for monitoring of medical apparatuses, in which the signals of the individual alarms of one apparatus are converted into understandable speech texts, is known from DE 33 02 321 A1.

In such a monitoring device, all alarm states of the individual apparatus are communicated to a monitoring person. However, a workstation in an intensive care unit has a plurality of medical patient monitoring devices, which can signal a correspondingly large number of alarms. The monitoring person receives all existing alarms independently of their importance. When alarms appear simultaneously, delays may occur in perception on the part of the monitoring person, because the alarm signals must first be converted into the corresponding speech text. A vitally important alarm signal pertaining to the patient may thus only be recognized with a delay.

SUMMARY OF THE INVENTION

The basic object of the present invention is to provide a monitoring system for monitoring various medical apparatuses, which informs the monitoring personnel of the most important alarm signals occurring in the particular situation rapidly and reliably in a specific manner.

According to the invention, a monitoring system for medical apparatuses is provided including a first medical apparatus and second medical apparatus which can each send at least one alarm signal. An alarm unit is connected to the first medical apparatus and the second medical apparatus. The alarm unit has at least one processing unit, a memory unit and an output unit. The processing unit assigns priorities to alarm signals. An assignment list is provided that has a distribution of the priorities of the individual alarm signals. The assignment list is stored in the memory unit.

The priorities of the individual alarm signals may include highest priority alarm signals and only the highest priority alarm signals may be sent via the output unit. The alarm signals produce alarms sent visually and/or audibly. The alarm signals may be sent corresponding to a user list stored in the memory unit.

According to another aspect of the invention, a process is provided for processing at least one alarm signal from each of at least two medical apparatuses. With reception of an alarm signal of a first apparatus there is an identification of the alarm signal of the first apparatus and an assignment of a priority to the alarm signal and an assignment of the alarm signal of the first apparatus to an alarm class. These steps are repeated for the alarm signal of the second or every other apparatus.

At least one first and one second alarm class are provided, the first alarm class having a low alarm priority and the second alarm class having a higher alarm priority. The alarm signals of the alarm class with the higher alarm priority are sent.

The alarm signals within one alarm class may be prioritized. When at least two of the alarm signals of the same alarm class are present, the alarm signal with the respective higher assigned priority is sent. The alarm signals are sent (issued) visually and/or audibly.

The process further allows the possibility of the individual alarms being assigned to certain user groups. The alarms that can be assigned to a particular user group are sent to the respective user group.

The essential content of the present invention is that various types of alarm signals of the various apparatuses are prioritized and a uniform alarm management is thus created for a medical workstation having a plurality of apparatuses.

The advantages gained with the present invention are especially that any alarm signal can be assigned to an adequate alarm class corresponding to its significance for preserving the life of the patient by the process steps according to the present invention, namely, a) reception of an alarm signal of a first apparatus; b) identification of the alarm signal of the first apparatus; c) assignment of a priority to the alarm signal; d) assignment of the alarm signal of the first apparatus to an alarm class; and e) repetition of steps a) through d) for an alarm signal of a second or any other apparatus. In a preferred embodiment of the process according to the present invention, at least one first alarm class and one second alarm class are provided, the first alarm class having a low alarm priority and the second alarm class having a higher alarm priority, and the signals of the alarm class with the higher alarm priority are sent. A very high alarm priority characterizes a life-threatening state of the patient, to the signaling and rapid recognition of which the highest significance is to be assigned for the monitoring person. This may be, for example, respiratory arrest or cardiac arrest. The monitoring persons can thus initiate vitally necessary measures for a patient rapidly and in a specific manner. Alarm classes with a lower alarm priority contain alarms which do not represent a life-threatening state of the patient. These may be technical alarms, for example, the need to calibrate a sensor at a regular time interval intended therefor.

It may definitely happen with the process and system that two different alarm signals of, for example, two different medical apparatuses are assigned to the same alarm class. Provisions are made for this case in another embodiment of the present invention for the particular alarm signals to be prioritized within the same alarm class. The alarm signal with the higher prioritization will subsequently be sent. This may happen for the particular fields of application in the form of an alarm signal priority plan, which defines the priority and the sequence of sending the particular alarm signal of the same alarm class for the corresponding situation. After assigning the priorities to the alarm signals of one alarm class, assignment to different alarm levels can take place within the alarm class.

The process according to the present invention provides, furthermore, for the particular alarms to be able to be assigned to certain user groups. For example, in case of application in intensive care medicine, an alarm signal occurring when the respiration pressure exceeds or drops below a certain respiration pressure can be assigned to an anesthesiologist, and an alarm signal occurring when the parameters of an electro cardiogram (ECG) recording exceed or drop below certain values can be assigned to a surgeon. Thus, only the alarms necessary for a particular user group can be advantageously sent to the particular user group. For example, the surgeons does not receive all alarms any longer, but only those that are necessary for the surgeon.

Exemplary embodiments of the present invention are described in the Figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
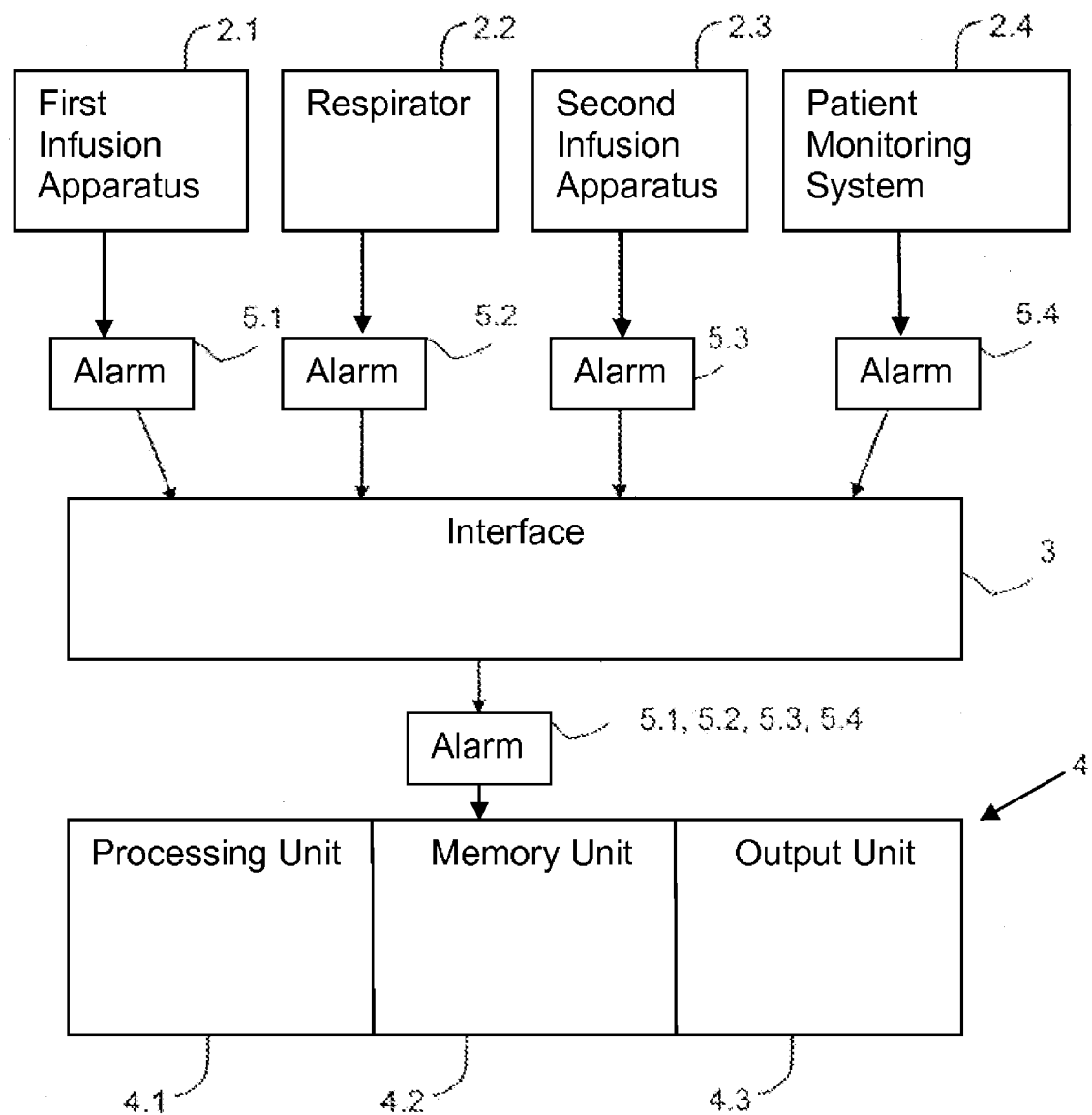
FIG. 1 is a system according to the present invention.

Referring to the drawings in particular, FIG. 1 shows a monitoring system for medical apparatuses 2.1, 2.2, 2.3, 2.4, which comprises a first infusion apparatus 2.1, a respirator 2.2, a second infusion apparatus 2.3 and a patient monitoring system 2.4, which are used, for example, at a workstation in an intensive care unit. The infusion apparatuses 2.1 and 2.3 supply the patient with drugs, food and other solutions via an intravenous access. The respirator 2.2 supports the spontaneous breathing of the patient when needed or replaces it altogether. The apparatuses 2.1, 2.2, 2.3, 2.4 listed are connected to an alarm unit 4 each and deliver a great variety of alarm signals 5.1, 5.2, 5.3, 5.4. The alarm unit 4 contains a processing unit 4.1, a memory unit 4.2 and an output unit 4.3. The individual alarms 5.1, 5.2, 5.3, 5.4 are sent on the output unit 4.3 visually and/or audibly. The apparatuses 2.1, 2.2, 2.3, 2.4 are preferably represented as graphic symbols on the output unit 4.3 of the alarm unit 4. A corresponding symbol, which is graphically arranged on the output unit 4.3, is assigned to each apparatus 2.1, 2.2, 2.3, 2.4 connected to the alarm unit. As an alternative, the abbreviation of the name of the apparatus may be displayed as well. In another embodiment of the output unit 4.3 of the alarm unit 4, the current parameters of the individual apparatuses 2.1, 2.2, 2.3, 2.4 can be displayed and the apparatuses 2.1, 2.2, 2.3, 2.4 can be controlled via an addition unit, not shown. The alarm unit 4 is connected to the corresponding individual apparatuses 2.1, 2.2, 2.3, 2.4 via an interface 3. The interface 3 is designed as a bidirectional data interface 3 for reliable communication. To prevent an incorrect function of the alarm unit 4 from leading to suppression of an alarm 5.1, 5.2, 5.3, 5.4 on one of the individual apparatuses 2.1, 2.2, 2.3, 2.4, the alarm unit 4 acknowledges the receipt of the alarm 5.1, 5.2, 5.3, 5.4. When no acknowledgment is sent by the alarm unit 4, an alarm is triggered at the device 2.1, 2.2, 2.3, 2.4, from which the alarm 5.1, 5.2, 5.3, 5.4 had been sent. In addition, satisfactory function of the interface 3 is monitored. Interruption of the connection leads to the triggering of a high-priority alarm on the alarm unit 4. It can thus be prevented that alarms 5.1, 5.2, 5.3, 5.4 of the apparatuses 2.1, 2.2, 2.3, 2.4 are not received or not output by the alarm unit 4. In another embodiment of the monitoring system according to the present invention, changes made on the apparatuses 2.1, 2.2, 2.3, 2.4, for example, a change of an alarm limit, can be automatically documented. The parameters of the changes are stored for this purpose in the memory unit 4.2 of the alarm unit 4.

If the infusion apparatus 2.1 now sends an alarm 5.1 as a consequence of an excessively low flow rate, the processing unit 4.1 of the alarm unit 4 evaluates the alarm 5.1 and assigns a priority to the alarm 5.1. The prioritization of the alarms may be stored in the memory unit 4.2 of the alarm unit 4 in the form of an alarm list, which contains an alarm plan. The individual alarms can be better adapted to one another and to the different alarm situations with an alarm plan. According to the assigned priority, the alarm 5.1 is grouped by the processing unit 4.1 to a corresponding alarm class AC1, AC2. Different alarm classes AC1, AC2 may be defined. For example, three alarm classes may be provided, the alarm class with the highest priority characterizing a life-threatening state of the patient, the alarm class with the medium priority a serious state of the patient and the alarm class with the lowest alarm priority being noncritical for the patient's state. If there is simultaneously or sequentially another alarm 5.2, for example, from the respirator 2.2 as a consequence of apnea of the patient, this alarm 2.2 is likewise evaluated by the processing unit 4.1. Very high priority is assigned to this alarm 5.2 by the processing unit 4.1, because it represents a life-threatening state for the patient. The output unit 4.3 always sends the alarm of the highest alarm class, in this case the alarm 5.2 of the respirator 2.2. All the others that are not output directly by the output unit 4.3 but continue to be present are stored in the memory unit 4.2 and can be polled from same. After eliminating the cause of the alarm and after the alarm has been acknowledged by the monitoring person, an alarm of a lower alarm class, i.e., the alarm 5.1 of the infusion apparatus 2.1 related to an excessively low flow rate is output by the output unit 4.3 if the cause of the alarm 5.1 has not yet been eliminated.

Prioritization of the alarms 5.1, 5.2, 5.3, 5.4 is performed with the monitoring system according to the present invention, so that alarms 5.1, 5.2, 5.3, 5.4 are grouped in alarm classes AC1, AC2 and the sending of these alarms is also set on the output unit 4.3. If two alarms 5.1, 5.2, 5.3, 5.4 arrive at the alarm unit 4, which are grouped by the processing unit 4.1 to the same alarm class AC1, AC2, i.e., for example, the patient monitoring system 2.4 signals an alarm 5.4 as a consequence of an excessively high blood pressure and the respirator 2.2 an alarm 5.2 as a consequence of an excessively high airway pressure, a further prioritization of the alarms 5.2 and 5.4 is performed by the processing unit 4.1. The alarm that is more vitally important for the patient, i.e., the alarm 5.4 triggered as a consequence of the excessively high blood pressure, is given a higher priority within the alarm class. This means that the alarm 5.4 of the excessively high blood pressure is output by the output unit 4.3 before the alarms 5.2 as a consequence of an excessively high airway pressure is signaled. The prioritization of the alarms 5.1, 5.2, 5.3, 5.4 can in turn be stored in the memory unit 4.2 of the alarm unit 4 in the form of an alarm list.

If the respirator 2.2 signals, in another example, an alarm 5.2 as a consequence of an excessively low minute volume and the patient monitoring system 2.4 signals an alarm 5.4 as a consequence of an excessively low oxygen saturation, a higher priority is assigned by the processing unit 4.1 to the alarm 5.4 within the same alarm class in this case because the oxygen saturation is the more vitally important parameter for the patient. The patient has a respiratory arrest already existing for a rather long time without an apnea backup ventilation having been set. The monitoring persons can thus rapidly initiate a step necessary for preserving the patient's life.

In another embodiment variant of the monitoring system according to the present invention, not shown, the alarms 5.1, 5.2, 5.3, 5.4 of the individual alarm classes AC1, AC2 are selectively assigned to certain user groups. An assignment list or look up table is stored for this in the memory unit 4.2 of the alarm unit 4. For example, the anesthesiologist needs a different amount of alarm information than the surgeon in an intensive care unit operating room, because the two users have different priorities in performing their work. For example, the anesthesiologist needs the alarm 5.2 triggered in case of deviation of the ventilation parameters set on the respirator 2.2, whereas the surgeon needs the alarm 5.4 occurring in case of deviation of the heart rate of the patient monitoring system 2.4.

Figure 2:
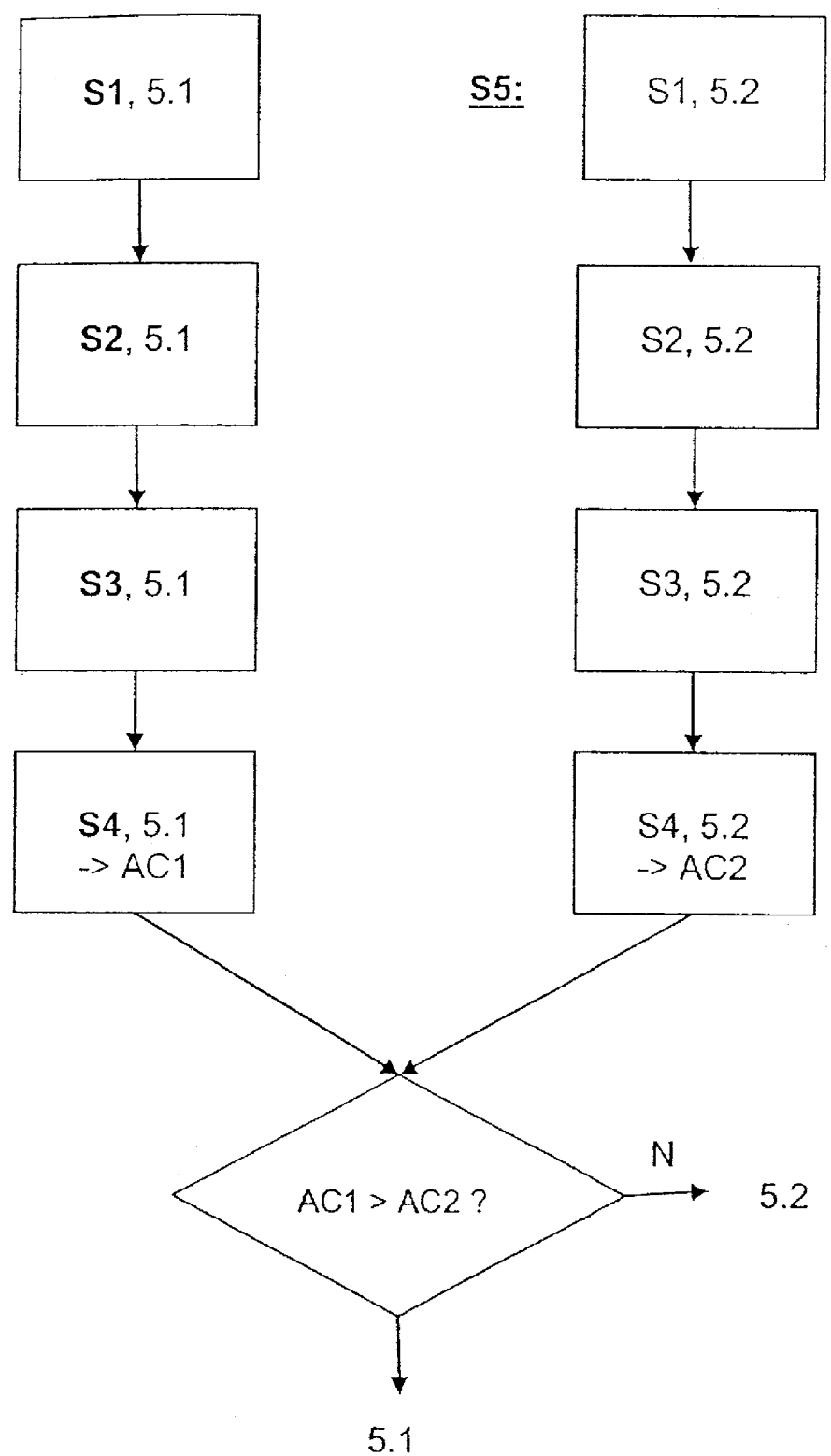
FIG. 2 is a flow diagram showing the course of a process according to the present invention.

The individual steps S1, S2, S3, S4, S5 of the process according to the present invention are shown in FIG. 2 on the basis of the alarm signals 5.1 and 5.2. The process provides for the reception of the alarm signal 5.1 of a first apparatus 2.1 in a first step S1. An example of a monitoring system for medical apparatuses, with which the process steps S1 through S5 are carried out, was described above and is shown in FIG. 1. An alarm cause is recognized on an alarm-triggering apparatus 2.1, 2.2, 2.3, 2.4 and is passed on as an alarm 5.1, 5.2, 5.3, 5.4 to an alarm unit 4. The alarm unit 4 recognizes in a second Step S2 the apparatus among the apparatuses 2.1, 2.2, 2.3, 2.4 connected to the alarm unit 4 from which the alarm 5.1 is coming. In another step S3, a priority is assigned to the alarm signal 5.1 of the first apparatus 2.1, i.e., the alarm 5.1 is evaluated. Corresponding to the assigned priority, the alarm signal 5.1 is assigned to an alarm class AC1 in a fourth step S4. The number of alarm classes AC1, AC2 and which alarm 5.1, 5.2, 5.3, 5.4 can be assigned to which alarm class AC1, AC2 is set for the alarm unit 4. There are alarm classes with a low alarm priority and alarm classes with a higher alarm priority. In a fifth process step S5, the process steps S1 through S4 are repeated for another alarm signal 5.2 of a second apparatus 2.2. Consequently, an alarm 5.2 triggered on a second apparatus 2.2 is received by the alarm unit 4. The alarm unit 4 identifies the alarm signal 5.2 of the second apparatus 2.2, assigns a priority to it and assigns an alarm class AC2 to this alarm signal 5.2.

The alarm signal 5.1, 5.2, 5.3, 5.4 of the alarm class AC1, AC2 with the higher alarm priority is sent by the alarm unit 4. This may take place visually and/or audibly via output unit 4.3 of the alarm unit 4. For example, a graphic symbol assigned to the particular apparatus 2.1, 2.2, 2.3, 2.4 may be displayed with a colored background corresponding to the particular alarm class AC1, AC2, for example, in red marking in case of an alarm 5.1, 5.2, 5.3, 5.4 of the highest alarm class.

In a preferred embodiment of the process according to the present invention, the alarm signals 5.1, 5.2, 5.3, 5.4 of the same alarm class AC1, AC2 are prioritized in another step. The prioritization of the alarm signals 5.1, 5.2, 5.3, 5.4 of the same alarm class AC1, AC2 specifies the site in an alarm list at which the particular alarm signals 5.1, 5.2, 5.3, 5.4 are defined and which other alarm signals 5.1, 5.2, 5.3, 5.4 can and may cover them. Thus, only the alarm signal 5.1, 5.2, 5.3, 5.4 that is most important for preserving the patient's life is sent from the entirety of the arriving alarm signals 5.1, 5.2, 5.3, 5.4. This has the advantage that the number of audio alarms 5.1, 5.2, 5.3, 5.4 in an intensive care unit is reduced to a necessary level and the monitoring persons can remedy the patient's life-threatening situation in a concentrated manner and rapidly. In addition, the space of a display field is limited in case of visual output of an alarm signal 5.1, 5.2, 5.3, 5.4 and cumbersome "paging through" the alarms 5.1, 5.2, 5.3, 5.4 can be avoided. The prioritization of the alarm signals 5.1, 5.2, 5.3, 5.4 is steadily checked and rechecked. The user is thus relieved and can perform the procedures necessary for eliminating the cause of the alarm rapidly and in a specific manner. Prioritization of two alarms 5.1, 5.2, 5.3, 5.4 of the same alarm class will be described below. If, for example, a respirator 2.2 reports an alarm 5.2 as a consequence of an excessively high airway pressure and a patient monitoring system 2.4 at the same time reports an alarm 5.4 as a consequence of an excessively high blood pressure, the alarm 5.4 triggered as a consequence of the excessively high blood pressure is the more important alarm for preserving the patient's vital functions in this case and is set at a higher alarm priority. If a respirator 2.2 signals, in another exemplary embodiment, an alarm 5.2 on the basis of an excessively low minute volume and a patient monitoring system 2.4 an alarm 5.4 as a consequence of an excessively low oxygen saturation, the alarm based on the excessively low oxygen saturation is the more important alarm for preserving the patient's life in this case because the patient has a respiratory arrest that has already been present for a rather long time without an apnea back-up ventilation having been set. The alarm 5.4 receives the higher alarm priority.

While specific embodiments of the invention have been shown and described in detail to illustrate the application of the principles of the invention, it will be understood that the invention may be embodied otherwise without departing from such principles.

What is claimed is:

1. A monitoring system for medical apparatuses, the system comprising:
   a first medical apparatus and second medical apparatus which can each send at least one alarm signal;
   an alarm unit connected to said first medical apparatus and said second medical apparatus, said alarm unit having at least one processing unit, a memory unit and an output unit, said processing unit assigning priorities to alarm signals;
   an assignment list of the distribution of the priorities of the individual alarm signals, said assignment list being stored in said memory unit, wherein said at least one alarm signal of said first medical apparatus and said at least one alarm signal of said second medical apparatus are sorted into alarm classes based on said assignment list via said at least one processing unit; and
   a bidirectional interface, said alarm unit receiving said at least one alarm signal of said first medical apparatus and said at least one alarm signal of said second medical apparatus via said bidirectional interface, said alarm unit providing an alarm recognition signal as output to at least one of said first medical apparatus and said second medical apparatus when said alarm unit receives one or more of said at least one alarm signal of said first medical apparatus and said at least one alarm signal of said second medical apparatus, said alarm recognition signal corresponding to a state in which said alarm unit receives one or more of said at least one alarm signal of said first medical apparatus and said at least one alarm signal of said second medical apparatus, wherein an alarm is provided as output at one or more of said first medical apparatus and said second medical apparatus when at least one of said first medical apparatus and said second medical apparatus does not receive said alarm recognition signal from said alarm unit, wherein said priorities of the individual alarm signals include highest priority alarm signals and only said highest priority alarm signals are sent via said output unit.

2. A monitoring system in accordance with claim 1, wherein said alarm signals produce alarms sent visually and/or audibly.

3. A monitoring system in accordance with claim 1, wherein said alarm signals are sent corresponding to a user list stored in said memory unit.

4. A process for processing at least one alarm signal each from at least two medical apparatuses, the process comprising the steps of:
   a) receiving an alarm signal of a first apparatus;
   b) identifying the received alarm signal of the first apparatus;
   c) assigning a priority to the alarm signal identified of the first apparatus;
   d) assigning the alarm signal of the first apparatus to an alarm class based on step c;
   e) repeating steps a) through d) for an alarm signal of a second or every other apparatus; and
   providing a bidirectional interface, an alarm unit receiving said at least one alarm signal of said first medical apparatus and said at least one alarm signal of said second medical apparatus via said bidirectional interface, said alarm unit providing an alarm recognition signal as output to at least one of said first medical apparatus and said second medical apparatus when said alarm unit receives at least one of said at least one alarm signal of said first medical apparatus and said at least one alarm signal of said second medical apparatus, one or more of said first medical apparatus and said second medical apparatus receiving said alarm recognition signal via said bidirectional interface when said alarm unit receives at least one of said at least one alarm signal of said first medical apparatus and said at least one alarm signal of said second medical apparatus, said alarm recognition signal corresponding to said alarm unit receiving said at least one alarm signal of said first medical apparatus and said at least one alarm signal of said second medical apparatus, wherein an alarm is provided as output at one or more of said first medical apparatus and said second medical apparatus when at least one of said first medical apparatus and said second medical apparatus does not receive said alarm recognition signal from said alarm unit, wherein the alarm signals of the second alarm class with the higher alarm priority are sent to an alarm output before the signals of the first alarm class with the low alarm priority.

5. A process in accordance with claim 4, wherein at least one first alarm class and one second alarm class are provided, said first alarm class having a low alarm priority and the second alarm class having a higher alarm priority.

6. A process in accordance with claim 5, wherein said alarm signals are prioritized within one said alarm class.

7. A process in accordance with claim 6, wherein when at least two alarm signals of the same alarm class are present, said alarm signal with the respective higher assigned priority is sent.

8. A process in accordance with claim 4, wherein said alarm signals are sent visually and/or audibly.

9. A process in accordance with claim 4, wherein the individual alarms are assigned to certain user groups.

10. A process in accordance with claim 9, wherein said alarms that are assigned to a particular user group are sent to the respective user group.

11. A monitoring system for medical apparatuses, the system comprising:
   a first medical apparatus that can issue at least one alarm signal upon the occurrence of an alarm event;
   a second medical apparatus that can issue at least one alarm signal upon the occurrence of an alarm event;
   an alarm unit connected to said first medical apparatus and connected to said second medical apparatus, said alarm unit having at least one processing unit, a memory unit and an output unit for issuing an alarm based on one of the alarm signals;
   a look up table established in said memory, said look up table including an assignment of each alarm signal to a priority class, said alarm unit issuing visual and/or audible alarms through said output unit based on the priority class for a corresponding alarm signal, wherein said at least one alarm signal of said first medical apparatus and said at least one alarm signal of said second medical apparatus are sorted into alarm classes based on said look up table via said at least one processing unit, wherein at least one alarm signal of said first medical apparatus and said at least one alarm signal of said second medical apparatus are prioritized within one said alarm class; and
   a bidirectional interface, said alarm unit receiving said at least one alarm signal of said first medical apparatus and said at least one alarm signal of said second medical apparatus via said bidirectional interface, said alarm unit providing an alarm recognition signal as output to at least one of said first medical apparatus and said second medical apparatus when said alarm unit receives at least one of said at least one alarm signal of said first medical apparatus and said at least one alarm signal of said second medical apparatus, one or more of said first medical apparatus and said second medical apparatus receiving said alarm recognition signal via said bidirectional interface when said alarm unit receives one or more of said at least one alarm signal of said first medical apparatus and said at least one alarm signal of said second medical apparatus, said alarm recognition signal corresponding to said alarm unit receiving one or more of said at least one alarm signal of said first medical apparatus and said at least one alarm signal of said second medical apparatus, wherein an alarm is provided as output at one or more of said first medical apparatus and said second medical apparatus when at least one of said first medical apparatus and said second medical apparatus does not receive said alarm recognition signal from said alarm unit, wherein said priorities of the individual alarm signals include highest priority alarm signals and only said highest priority alarm signals are sent via said output unit to issue an alarm.

12. A monitoring system in accordance with claim 11, further comprising: a user list established in said memory, each user of said user list being associated with a device operatively connected to said alarm unit, said user list including an assignment of each alarm signal to one or more users wherein alarms are issued through said output unit and directed to one or more of said users or sent to one or more connected devices based on the association of an alarm signal in said user list.

13. A monitoring system in accordance with claim 11, wherein said processor builds an alarm table in said look up table by identifying an initially received alarm signal of an apparatus, assigning a priority to the alarm signal identified, assigning the alarm signal to an alarm class based on the assigned priority and saving the assigned priority and alarm class.

14. A monitoring system in accordance with claim 11, wherein at least one first alarm class and one second alarm class are provided, said first alarm class having a low alarm priority and the second alarm class having a higher alarm priority, wherein the alarm signals of the second alarm class with the higher alarm priority are sent to said alarm output before the signals of the first alarm class with the low alarm priority.

15. A monitoring system in accordance with claim 11, wherein when at least two alarm signals of the same alarm class are present, said alarm signal with the respective higher assigned priority is sent.

16. A monitoring system in accordance with claim 11, wherein said look up table is established in said memory based on a preset assignment of each alarm signal to a priority class.

17. A process for processing at least one alarm signal each from at least two medical apparatuses, the process comprising the steps of:
   providing a first medical apparatus, said first medical apparatus providing a first medical apparatus alarm signal as output;
   providing a second medical apparatus, said second medical apparatus providing a second medical apparatus alarm signal as output;
   providing a bidirectional interface;
   providing an alarm unit, said alarm unit having at least one processing unit, a memory unit and an output unit, said at least one processing unit:
      a) receiving said first medical apparatus alarm signal via said bidirectional interface;
      b) identifying said first medical apparatus alarm signal;
      c) assigning a priority to said first medical apparatus alarm signal;
      d) assigning said first medical apparatus alarm signal to an alarm class based on step c;
      e) repeating steps a) through d) for said second medical apparatus alarm signal;
   providing an alarm recognition signal as output to at least one of said first medical apparatus and said second medical apparatus via said alarm unit when said at least one processing unit receives at least one of said first medical apparatus alarm signal and said second medical apparatus alarm signal, wherein at least one of said first medical apparatus and said second medical apparatus receives said alarm recognition signal via said bidirectional interface;
   providing an alarm as output at one or more of said first medical apparatus and said second medical apparatus when at least one of said first medical apparatus and said second medical apparatus does not receive said alarm recognition signal from said alarm unit.

* * * * *